(12) United States Patent
Lee et al.

(10) Patent No.: US 6,379,743 B1
(45) Date of Patent: Apr. 30, 2002

(54) PROCESS FOR THE PREPARATION OF ORGANIC ELECTROLUMINESCENT DEVICE USING VAPOR DEPOSITION POLYMERIZATION

(75) Inventors: Jae-Gyoung Lee, Kyounggi-do; Youngkyoo Kim, Pusan; Dong-Kwon Choi, Seoul, all of (KR)

(73) Assignee: NessDisplay, Co. Ltd., Suwon-si (KR)

( * ) Notice: Subject to any disclaimer, the term of this patent is extended or adjusted under 35 U.S.C. 154(b) by 0 days.

(21) Appl. No.: 09/768,160

(22) Filed: Jan. 24, 2001

Related U.S. Application Data

(62) Division of application No. 09/168,933, filed on Oct. 9, 1998, now abandoned.

(30) Foreign Application Priority Data

| | | |
|---|---|---|
| Oct. 10, 1997 | (KR) | 97-52097 |
| Oct. 10, 1997 | (KR) | 97-52099 |
| Oct. 13, 1997 | (KR) | 97-52337 |
| Mar. 4, 1998 | (KR) | 98-7040 |
| Jun. 23, 1998 | (KR) | 98-23644 |
| Sep. 17, 1998 | (KR) | 98-38469 |

(51) Int. Cl.$^7$ .............................. B05D 5/12; B05D 5/06
(52) U.S. Cl. .............................. 427/66; 427/69; 427/70; 427/164
(58) Field of Search ........................ 427/66, 164, 69, 427/70

(56) References Cited

U.S. PATENT DOCUMENTS

| | | | | |
|---|---|---|---|---|
| 4,769,292 A | * | 9/1988 | Tang et al. | 428/690 |
| 5,443,921 A | * | 8/1995 | Hosokawa et al. | 428/690 |
| 5,837,166 A | * | 11/1998 | Kawamura et al. | 252/583 |
| 5,847,506 A | * | 12/1998 | Nakayama et al. | 313/112 |
| 6,013,982 A | * | 1/2000 | Thompson et al. | 313/506 |
| 6,111,697 A | * | 8/2000 | Merrill et al. | 359/490 |

FOREIGN PATENT DOCUMENTS

| | | |
|---|---|---|
| JP | 2-230583 | 10/1991 |
| JP | 3-274693 | 12/1991 |
| JP | 4-73886 | 3/1992 |
| JP | 7-11249 | 1/1995 |
| JP | 9-153641 | 6/1997 |
| JP | 9-180833 | 7/1997 |
| WO | WO 94/07334 | 3/1994 |

\* cited by examiner

*Primary Examiner*—Shrive P. Beck
*Assistant Examiner*—Michael Cleveland
(74) *Attorney, Agent, or Firm*—Jacobson Holman, PLLC

(57) ABSTRACT

A process for preparing an organic electroluminescent device having a transparent substrate, a transparent electrode layer, a metallic electrode layer, and an organic interlayer containing an electronically active material dispersed in a matrix of polyimide, characterized in that the organic interlayer is prepared by depositing the vapors of a dianhydride, a diamine and the electronically active material to form a polyimide precursor layer containing the active material dispersed therein and thermally imidizing the polyimide precursor layer. The organic luminescent device thus obtained has improved luminous efficiency, thermal stability, interfacial surface roughness and high bulk density of the layer.

1 Claim, 5 Drawing Sheets

PROCESS FOR THE PREPARATION OF ORGANIC ELECTROLUMINESCENT DEVICE USING VAPOR DEPOSITION POLYMERIZATION

This is a divisional application of prior application Ser. No. 09/168,933 filed Oct. 9, 1998 now abandoned.

FIELD OF THE INVENTION

The present invention is directed to a process for the preparation of an organic electroluminescent device; and, more particularly, to a process for the preparation of an organic electroluminescent device containing a polyimide thin layer having an improved thermal stability, surface uniformity, and high density by way of vapor deposition polymerization.

BACKGROUND OF THE INVENTION

Generally, an organic electroluminescent device has a laminated structure comprising a transparent electrode layer, a metallic electrode layer, and an organic interlayer including an organic luminescent layer arranged between the two electrodes. The organic electroluminescent device can be operated with an alternating current(AC) or direct current (DC) power supply. In case of DC operation, the transparent electrode functions as an anode, and the metallic electrode as a cathode. In order to increase the luminance efficiency, the organic interlayer may further include hole transport agents and electron transport agents, often in a multilayer configuration.

For example, in case of DC operation, a separate hole transport layer may be disposed between, and in close contact with, the anode layer and one surface of the organic luminescent layer. Further, an optional electron transport layer may be placed between the cathode layer and the organic luminescent layer. Depending on the organic materials employed, therefore, the organic interlayer of an organic electroluminescent device may be in the form of single, double or triple layers, each layer containing various combinations of electronically active materials, i.e., organic luminescent materials, hole transport agents and electron transport agents. As the anode layer, indium tin oxide-glass layer is usually used while a metallic layer of magnesium, aluminum, indium or silver-magnesium can be used as the cathode.

In conventional organic electroluminescent devices, the organic layers are usually formed by vapor-depositing an active material such as a hole transport agent and organic luminescent material. However, an organic layer, e.g., a hole transport layer, prepared by a conventional vapor deposition method of an electronically active material, e.g., a hole transport material, has disadvantages in that the deposited organic layer is fragile and easily broken by a vibrational shock and the active material is often recrystallized because of the low glass transition temperature of the active material. For example, the glass transition temperature of N,N'-diphenyl-N,N'-bis(3-ethylphenyl)-1,1'-diphenyl-4,4'-diamine, one of the hole transport agents is about 63° C. Further, the lifetime of the device may be shortened due to the occurrence of recrystallization and diffusion migration phenomena during its use.

In order to solve the above problems, an organic layer has been prepared by dispersing an active material in a polymer matrix by a wet process such as spin coating using an organic solution thereof. However, the organic layer thus obtained has the deficiencies of surface roughness, low bulk density and contamination by residual organic solvent. Further, when the organic interlayer is of a multiple layer form, the interlayer adhesion is not sufficiently high, leading to a deteriorated interfacial contact and decreasing lifetime of the device. Moreover, it is difficult to accurately control the thickness of an organic layer by a conventional wet process and the reproducibility of the process is low, which may, in turn, result in poor performance of the device.

Therefore, there has existed a need to develop a process for the preparation of an organic electroluminescent device having an improved interfacial surface roughness, high bulk density, thermal stability and improved interfacial contact.

SUMMARY OF THE INVENTION

Accordingly, it is a primary object of the present invention to provide a process for preparing an organic electroluminescent device containing an organic interlayer having an improved surface roughness, high bulk density, thermal stability and improved interfacial contact.

In accordance with the present invention, there is provided a process for preparing an organic electroluminescent device having a transparent substrate, a transparent electrode layer, a metallic electrode layer, and an organic interlayer disposed between and in close contact with the electrode layers, the organic interlayer being comprised of an organic luminescent layer, an optional hole transport layer and an optional electron transport layer and containing an electronically active material dispersed in a matrix of polyimide of formula (I), characterized in that the organic interlayer is prepared by: i) depositing the vapors of a dianhydride, a diamine and the electronically active material to form a polyimide precursor layer containing the active material dispersed therein; and ii) thermally imidizing the polyimide precursor layer:

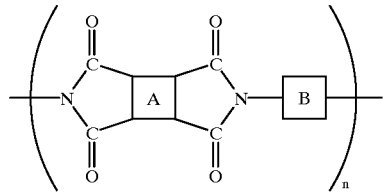

wherein A is derived from a dianhydride; B is derived from a diamine; and n is an integer of 2 or higher.

BRIEF DESCRIPTION OF THE DRAWINGS

The above and other objects and features of the present invention will become apparent from the following description thereof, when taken in conjunction with the accompanying drawings wherein:

FIG. 3-2: after thermal imidization);

FIGS. 4-1 and 4-2 depict atomic force microscopic spectra of the surface morphologies of a commercial deposited ITO layer and the hole transport layer formed in Example 2 of the present invention, respectively; and

Figure 5:
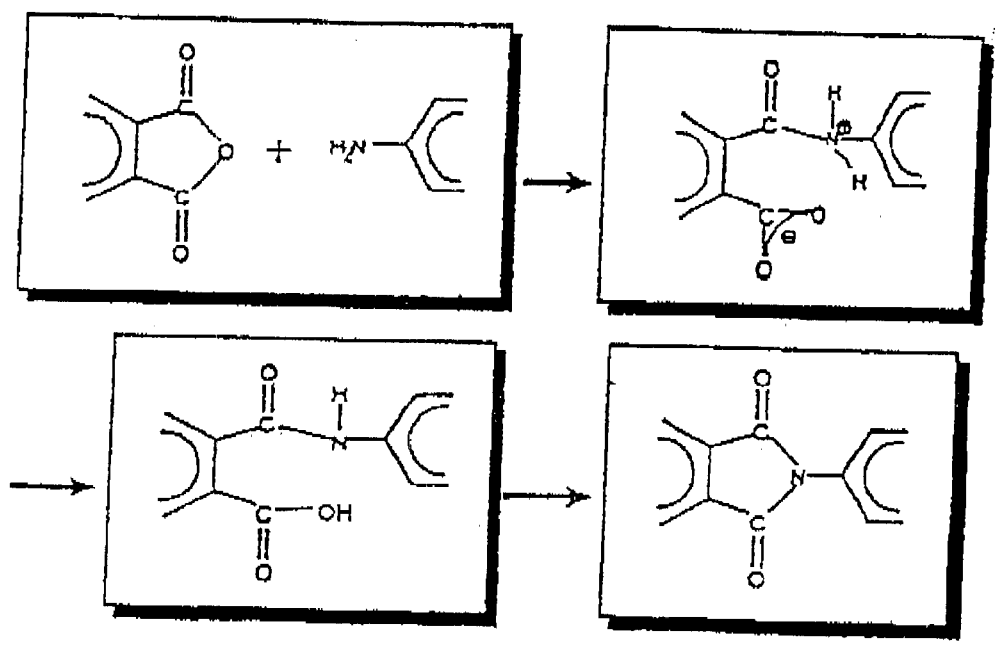

FIG. 5 shows the reaction of pyromellitic dianhydride (PMDA) with 4,4-oxyphenylene diamine(ODA).

DETAILED DESCRIPTION OF THE INVENTION

The organic electroluminescent device prepared in accordance with one aspect of the present invention comprises a transparent electrode layer prepared by etching an ITO (indium tin oxide) layer coated on a transparent substrate such as glass in accordance with a predetermined pattern, a metallic electrode layer of aluminum, magnesium, calcium, silver or other metal and an organic interlayer including an organic luminescent layer disposed between, and in close contact with, the transparent electrode layer and the metallic electrode layer. The organic electroluminescent device of the present invention can be operated with an alternating current (AC) or direct current(DC) power source. In case of DC operation, the transparent electrode functions as an anode, and the metallic electrode as a cathode.

The organic interlayer may further include a hole transport layer sandwiched between the transparent electrode layer and the organic luminescent layer. The organic interlayer may still further include an electron transport layer inserted between the metallic electrode layer and the organic luminescent layer.

The organic interlayer can thus be made in the form of a single layer or multiple layers depending on the desired combination of electronically active materials. As used herein the term "an electronically active material" refers to one selected from the group consisting of an organic luminescent, a hole transport, an electron transport agents and a mixture thereof. For example, the organic interlayer may be in the form of double layers consisting of a hole transport/organic luminescent layer and an electron transport layer, or consisting of a hole transport layer and an organic luminescent/electron transport layer. The organic interlayer may also be in the form of triple layers consisting of a hole transport layer, an organic luminescent layer and an electron transport layer.

In practicing the present invention, a polyimide of formula (I) is used in at least one layer of the organic interlayer. The polyimide of the present invention is obtained by vapor deposition polymerization of a dianhydride of formula(II) and a diamine of formula(III).

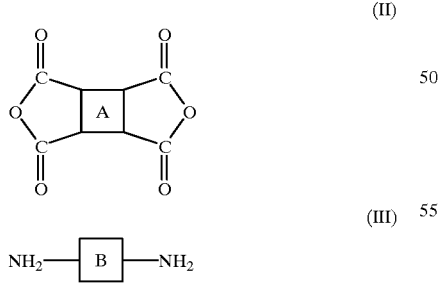

wherein A and B have the same meanings as defined above.

Exemplary dianhydrides of formula(II) include pyromellitic dianhydride(PMDA), 3,4,3',4'-biphenyltetracarboxylic dianhydride(BPDA), 3,3',4,4'-benzophenone tetracarboxylic dianhydride(BTDA), 4,4'-(hexafluoropropylidene) diphthalic anhydride(6FDA), 4,4'-(dimethylsilicon) diphthalic anhydride, 4,4'-oxydiphthalic anhydride(OPDA), 3,3',4,4'-diphenylsulfone tetracarboxylic dianhydride (DSDA),1,1'-bis(3,4-dicarboxylphenylanhydride)-1-phenyl-2,2,2-trifluoroethane(3FDA), 9,9'-bis (trifluoromethyl)-2,3,6,7-xanthene tetracarboxyl anhydride (6FCDA), terphenyl tetracarboxylic dianhydride(TPDA), 1,2,3,4-cyclopentane tetracarboxylic dianhydride, naphthalene-1,4,5,8-tetracarboxylic dianhydride, 3,4,9,10-perylene tetracarboxylic dianhydride, 4-(2,5-dioxotetrahydrofuran-3-yl)tetralin-1,2-dicarboxylic anhydride, 5-(2,5-dioxotetrahydrofuryl)-3-methyl-3-cyclohexene-1,2-dicarboxylicanhydride, bicyclo[2,2,2]oct-7-ene-2,3,5,6-tetracarboxylic dianhydride, 2,2'-di-tert-butylbiphenyl-bis(etherphthalic anhydride), 2,5-di-tert-butylphenyl-bis(etherphthalic anhydride) and bisphenol A-bis(etherphthalic anhydride). The structures of A in the polyimide of formula(I) derived from the above dianhydride are as follows:

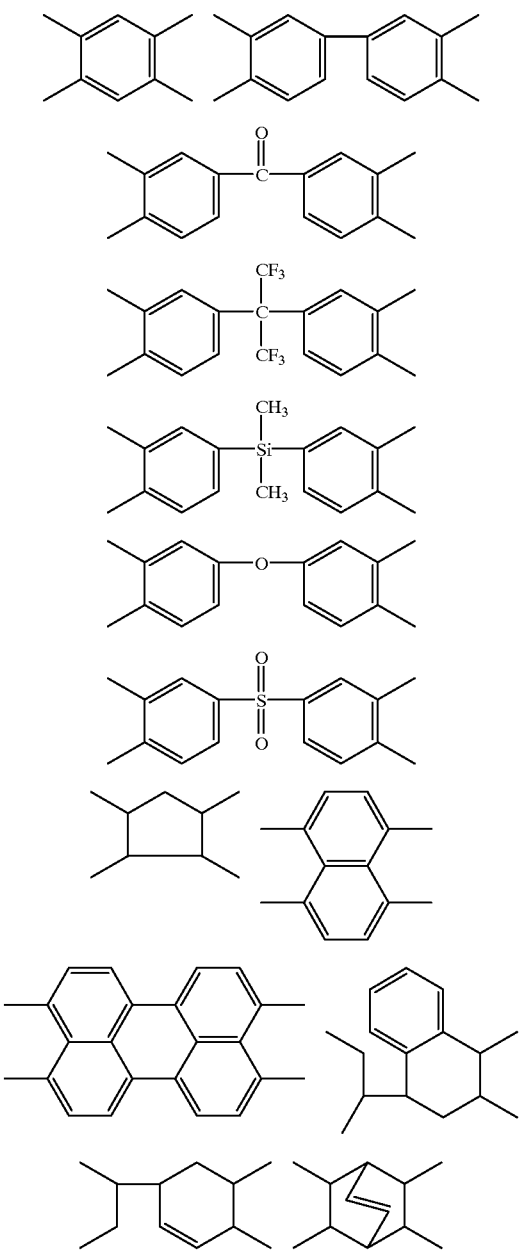

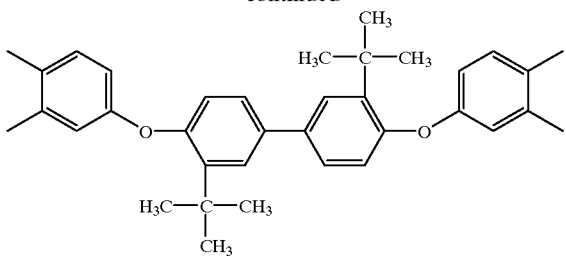

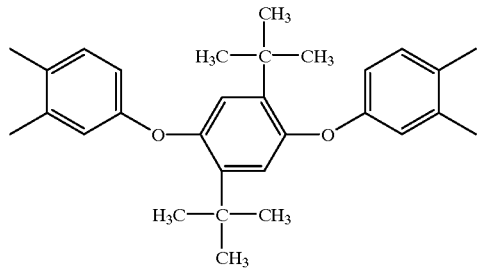

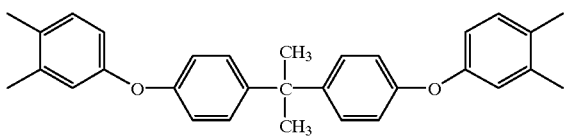

Representative diamines of formula(III) include 4,4'-oxydiphenylene diamine(ODA), p-phenylene diamine (PDA), 4,4'-diaminodiphenylmethane (4,4'-DDE), 3,4-diaminodiphenyl methane, 4,4-diaminodiphenyl methane (DDM), 2,2-bis (4-aminophenyl)propane, 2,2-bis(4-aminophenyl) hexafluoropropane(6FDAM), 1,1-bis (4-aminophenyl)- 1-phenyl-2,2,2-trifluoroethane(3FDAM), benzidine, 2,2-bis(trifluoromethyl)benzidine(TFMB), 1,3-bis(3-aminophenoxyl)benzene(APB), 3,5-diaminotoluene, 3,4-diaminodiphenylether, 3,4-diaminodiphenylmethane, 4,4'-phenylene diamine, 3,4-phenylene diamine, 3,3-diaminodiphenylether, 3,3'-diaminodiphenylmethane, 2,5-dimethyl-p-phenylene diamine, 2,3,5,6-tetramethyl-p-phenylene diamine, diaminofluorene, diaminofulorenone, 4,4'-diaminobenzophenone, 4,4'-diaminobiphenyl, 4,4'-diaminobibenzyl, 3,3'-diaminobenzophenone, 4,4'-diaminosulfide, α,α'-bis(4-aminophenyl)-1,4-diisopropylbenzene, 2,2-bis[4-(4-aminophenoxy)phenyl]-propane, 1,4-bis(4-aminophenoxy)benzene, 2,2-bis[4-(3-aminophenoxy)phenyl]hexafluoropropane, 2,2-bis[4-(4-aminophenoxy)phenyl]hexafluoropropane, 2,2-bis4-aminophenyl)hexafluoropropane, 1,4-bis(4-aminophenoxy)benzene, 2,6-diaminotoluene, mesitylene diamine, 4,4'-diaminodiphenylsulfone(DDS), 3,3'-diaminodiphenylsulfone, 3,3'-bis(aminophenyl)-hexafluoropropane, 2,2-bis(3-amino-4-hydroxylphenyl) hexa-fluoropropane, 4,4'-bis(2-chloroanilino)methane, 4,4'-bis(aminocyclohexyl)methane, 2,2'-bis(3-amino-4-methyl-phenyl)hexafluoropropane, 3,4'-diaminobenzophenone, 4,4'-diaminobibenzyl, 4,4'-bis(aminophenyl) hexafluoropropane, 1,3'-bis(m-aminophenoxy)benzene, 4,4'-methylene-bis-o-toluidine, 3,3'-diamino-4,4-dihydroxybiphenyl, 4,4'-diaminooctafluorodiphenyl, 4,4'-bis(aminophenyl)selenide, 9,10-bis(3-amino-phenylthio) anthracene, 9,10-bis(4-aminophenylthio)-anthracene, 9,10-bis( 3-aminoanilino)-anthracene, 9,10-bis(4-aminoanilino) anthracene, acridine yellow G, acriflavine, 3,6-diaminoacridine, 6,9-diamino-2-ethoxyacridine, basic fuchsin, methylated basic fuchsin, 2,4-diamino-6-phenyl-1,3,5-triazine, 9,10-diaminophen-5 anthrene, 3,8-diamino-6-phenylphenanthridine, dimidium bromide, ethidium bromide, propidium iodide, thionin, 3,7-diamino-5-phenylphenazium chloride and 3,3'-dimethylnaphthidine. The structures of B in the polyimide of formula(I) derived from the above diamines are as follows:

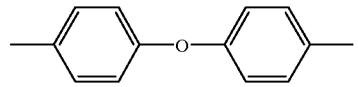

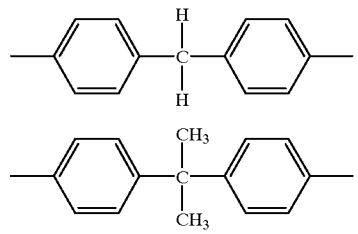

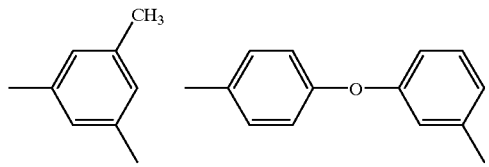

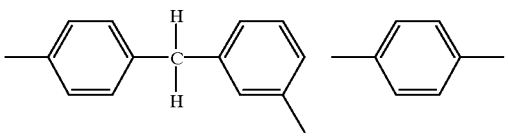

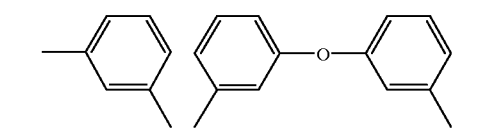

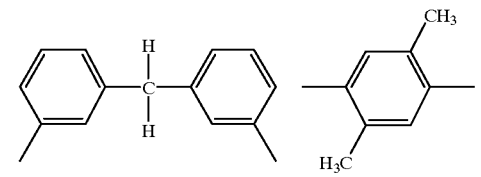

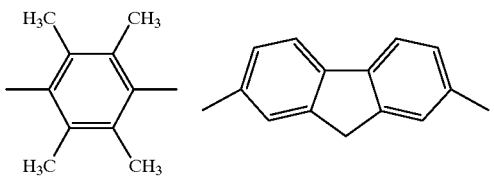

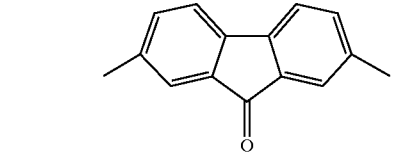

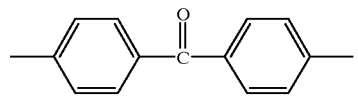

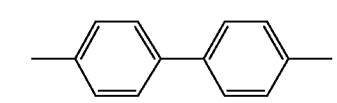

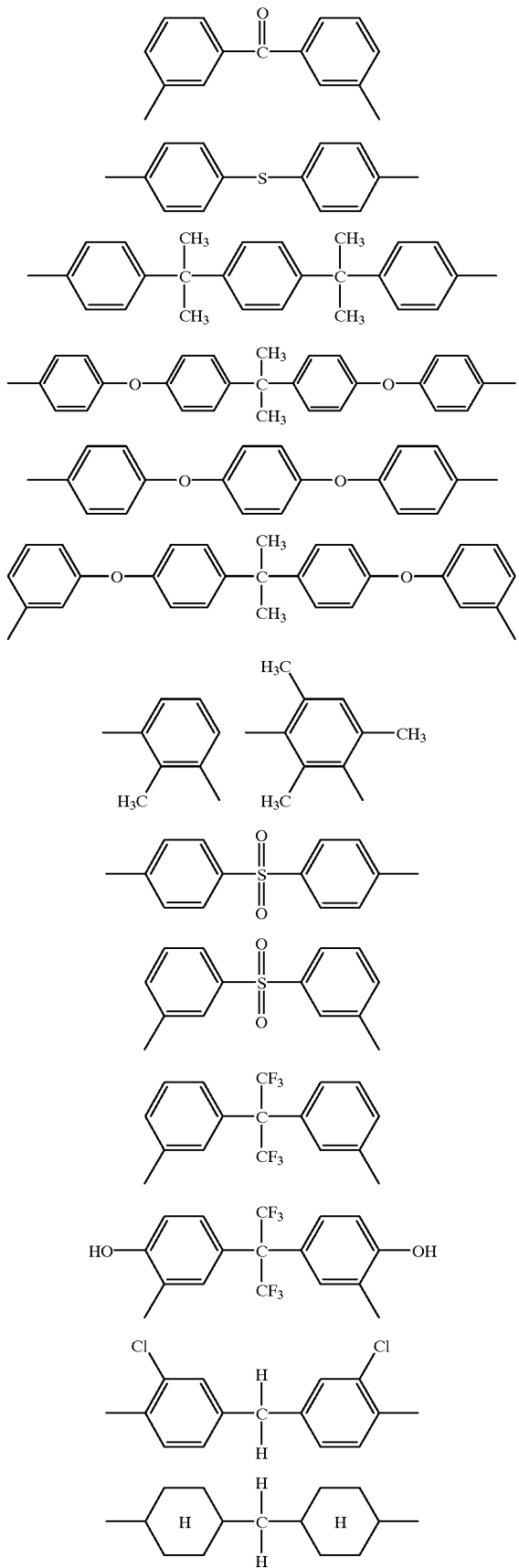
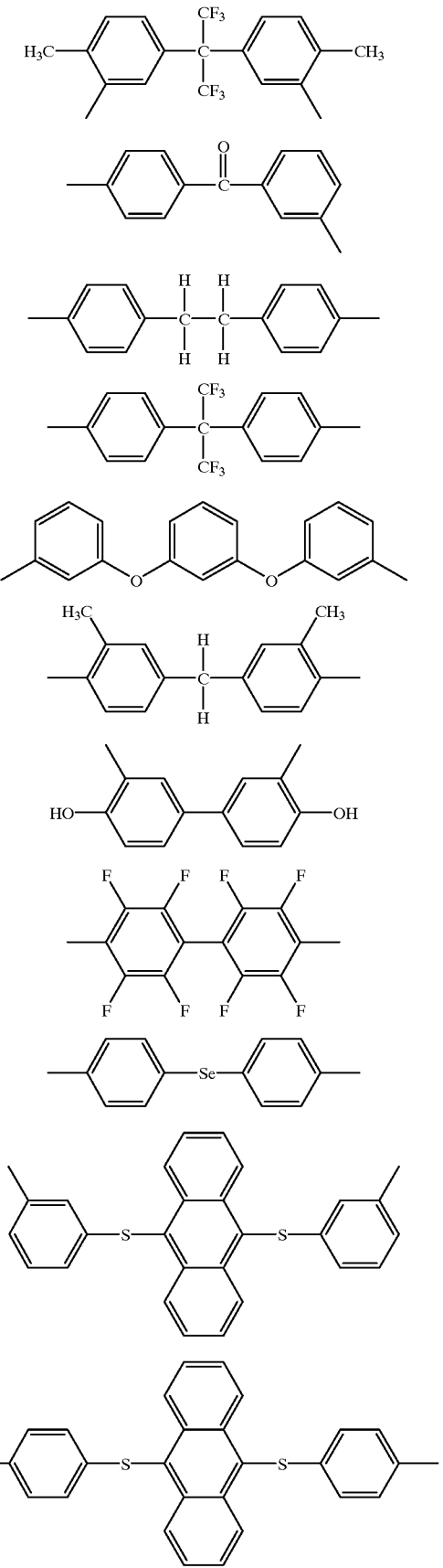

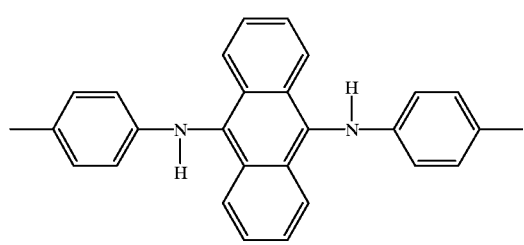
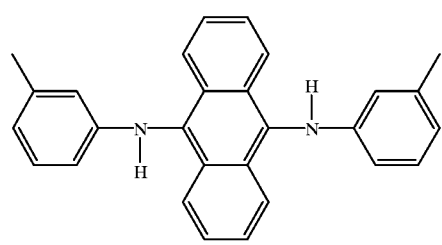
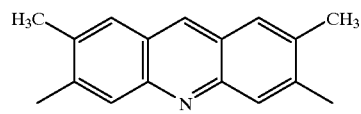
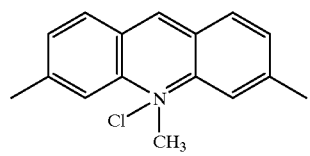
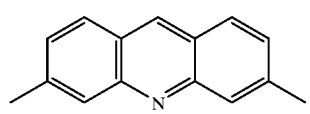
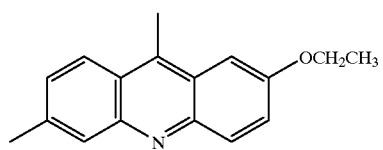
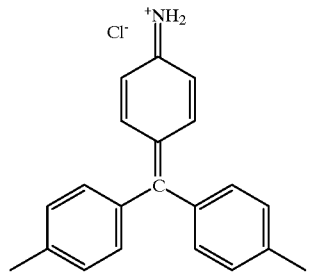
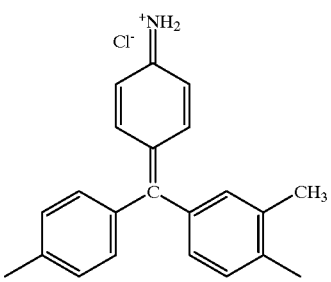
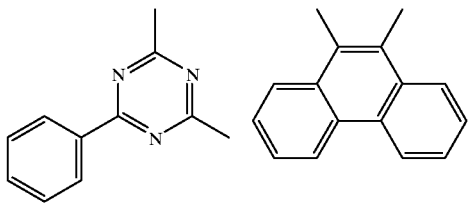
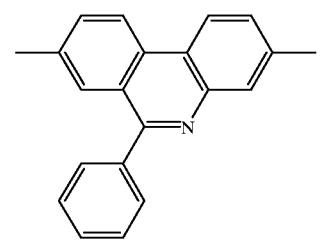
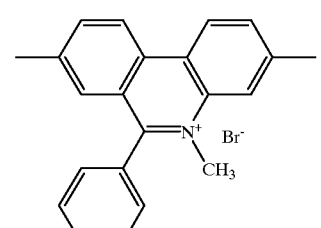
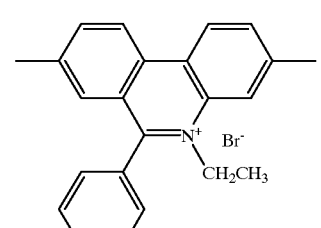
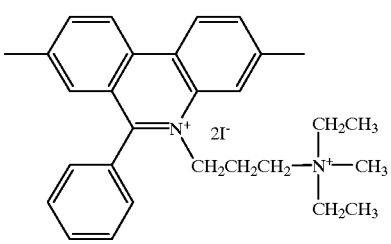
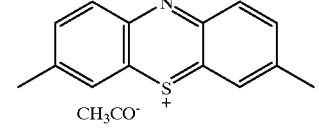
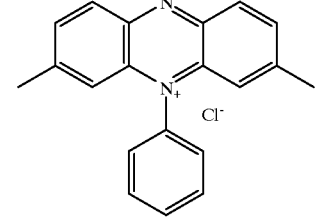

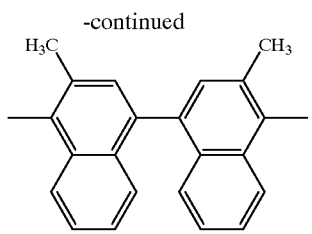

In the present invention, an organic interlayer is fabricated by vapor depositing a dianhydride and a diamine on a substrate or other organic layer together with an electronically active material to form a polyimide precursor such as a poly(amic acid) and thermally imidizing the polyimide precursor to obtain a polyimide layer wherein the active material is dispersed in the polyimide.

For example, the reaction of pyromellitic dianhydride (PMDA) and 4,4-oxyphenylene diamine(ODA) may be illustrated by FIG. 5.

FIG. 5, anhydride moiety of PMDA and amino moiety of ODA react to form a poly(amic acid) via a carboxylate intermediate, and then the poly(amic acid) is converted to a polyimide by thermal imidization. The polyimide film obtained by the vapor deposition polymerization method has lower surface roughness than that obtained by a conventional method.

The electronically active material used in the present invention is selected from the group consisting of a hole transport agent, organic luminescent material, electron transport agent and a mixture thereof.

In the vapor deposition polymerization process of the present invention, an electronically active material, a dianhydride and diamine are preferably deposited in a molar ratio ranging from 1:2:2 to 2:1:1 at a deposition rate ranging from 0.1 to 0.2 Å/sec, respectively.

Hole Transport Layer

A hole transport layer may be prepared by vapor depositing a conventional hole transport agent alone or by a conventional wet process. Preferably, it is prepared by vaporizing a hole transport agent, a dianhydride and a diamine to form a polyimide precursor layer containing the hole transport agent and thermally imidizing the polyimide precursor layer to fabricate a thin film wherein the hole transport agent is dispersed in a matrix of a polyimide of formula(I).

Exemplary hole transport agents include tertiary amines such as N,N'-diphenyl-N,N'-bis(3-methylphenyl)-1,1'-diphenyl-4,4'-diamine(TPD) of formula(IV), a diamine of formula(V), α-NPD of formula(VI), hydrazone of formula (VII), Cz-TPD of formula(VIII), TMDPAB of formula(IX), 4,4',4"-tris(3-methylphenylamino)triphenylamine(m-MTDATA) of formula(X) and compounds of formulae (XI) and (XII), among which TPD is preferred.

(IV)

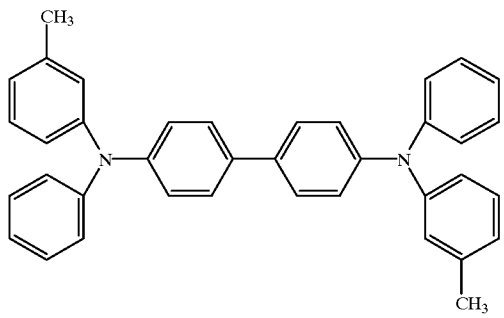

(V)

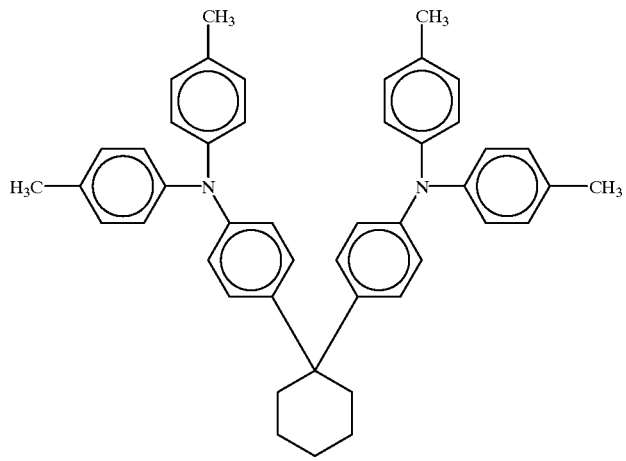

-continued
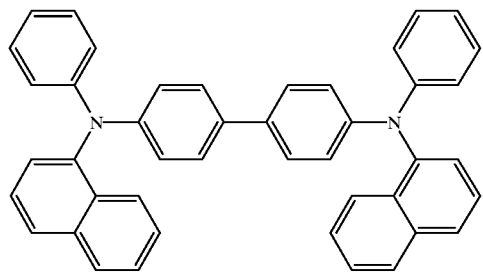
(VI)
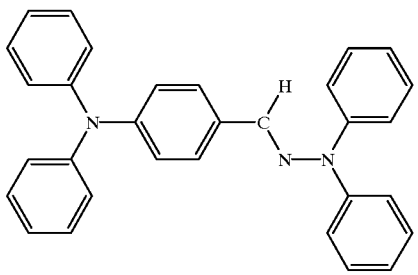
(VII)
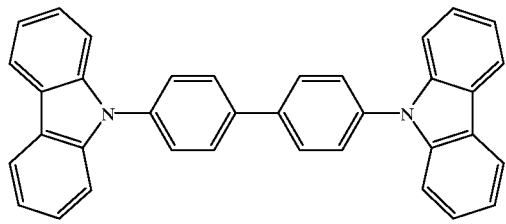
(VIII)
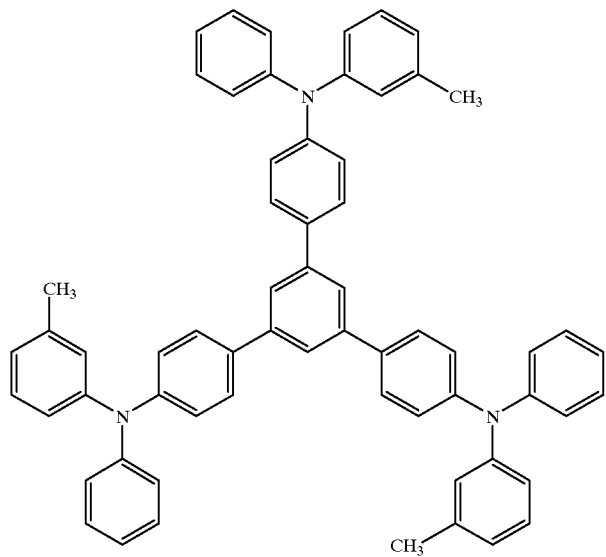
(IX)
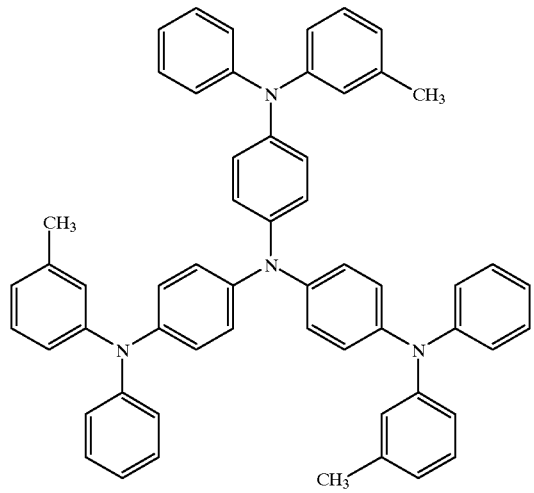
(X)

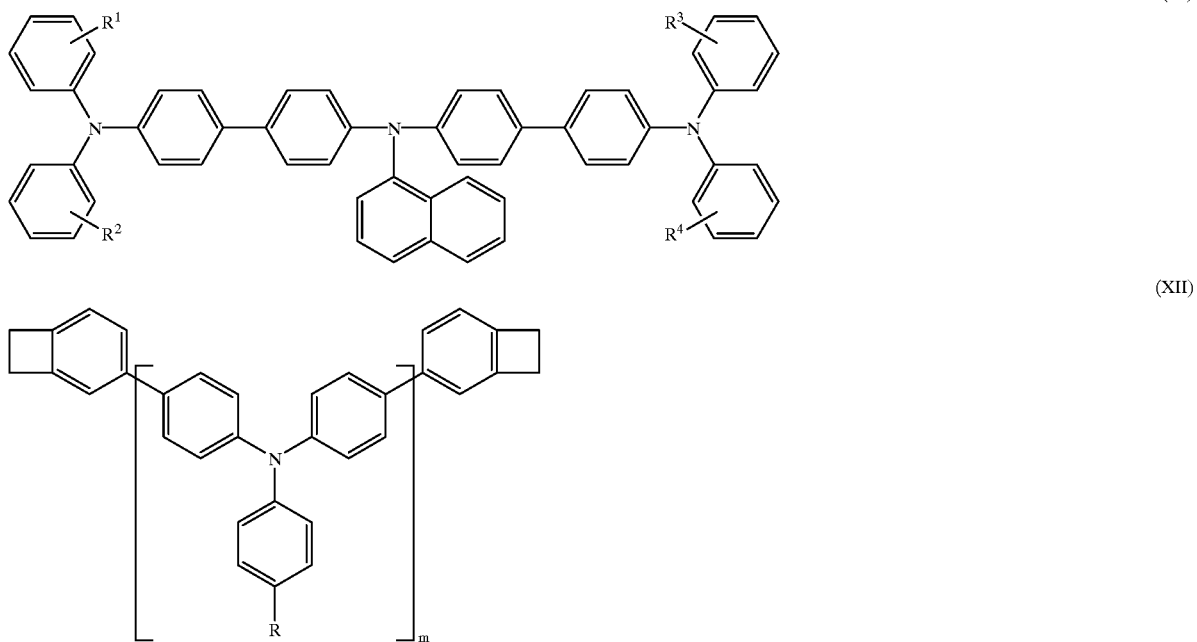

wherein, R, R¹, R² and R³ are each independently an alkyl or aromatic substitutent, and m is an integer of 1 or higher.

Particularly, when the polyimide matrix of the hole transport layer is made using a dianhydride having an electron affinity ranging from 1.10 to 1.90 eV, the luminous efficiency can be greatly increased. The electron affinities of some dianhydrides are shown in Table I.

The thickness of a hole transport layer ranges from 160 to 400 Å.

Organic Luminescent Layer

An organic luminescent layer may be prepared by vapor depositing a conventional electroluminescent material or by a conventional wet process. Preferably, it is prepared by vaporizing an electroluminescent material, a dianhydride and a diamine to form a polyimide precursor layer containing the electroluminescent material and thermal imidizing the polyimide precursor layer to fabricate a polyimide thin film wherein the electroluminescent material is dispersed in a matrix of a polyimide of formula(I).

Exemplary electroluminescent materials include tris(8-hydroxyquinolinolato) aluminum($Alq_3$), 1,1,4,4-tetraphenyl-1,3-butadiene(TB), oligophenylenevinylene derivatives, 4-(dicyanomethylene)-2-methyl-6-(4-dimethylaminostyryl)-4H-pyran(DCM), 1,4-distyrylbenzene, anthracene, tetracene, pentracene, coronene, perylene, pyrene, bis(8-quinolinolato) zinc(II), 9,10-diphenylanthracene, tris(4,4,4-trifluoro-1-(2-thienyl)-1,3-butandiono) -1,10-phenanthroline europium(III), tris(2,4-pentadiono)-1,10-phenanthroline terbium(III) and tris(4,4,4-trifluoro-1-(2-thienyl)-1,3-butandiono)-1,10-phenanthroline dysprosium(III).

The electroluminescent layer may be formed on an anode, or, when a hole transport layer is employed, on the surface of the hole transport layer.

The thickness of a organic luminescent layer ranges from 200 to 300 Å. The turn-on voltage of the present organic electroluminescent device can be controlled by varying the thickness of the organic luminescent layer.

Electron Transport Layer

An electron transport layer may be prepared by vapor depositing a conventional electron transport agent or by a conventional wet process. Preferably, it is prepared by vapor depositing an electron transport agent, a dianhydride and a diamine to form a polyimide precursor layer containing the electron transport agent and thermally imidizing the polyimide precursor layer to fabricate a thin film wherein the electron transport agent is dispersed in a matrix of a polyimide of formula(I).

Exemplary electron transport agents include oxadiazole derivatives such as 2-(4-biphenyl)-5-(4-tert-butylphenyl)-1,3,4-oxadiazole. The electron transport layer may be also formed on the organic luminescent layer.

When the polyimide matrix of an electron transport layer is made using a diamine having an ionization potential ranging from 6.80 to 7.70 eV, the luminous efficiency can be greatly increased. Ionization potentials of some diamines are shown in Table I.

TABLE I

| Dianhydride | Electron Affinity (eV) | Diamine | Ionization Potential (eV) |
|---|---|---|---|
| PMDA | 1.10 | ODA | 7.22 |
| BTDA | 1.55 | PDA | 6.88 |
| BPDA | 1.38 | 6FDAM | 6.80 |
| TPDA | 1.35 | 3FDAM | 6.92 |
| 6FDA | 1.33 | benzidine | 7.01 |
| ODPA | 1.30 | APB | 6.85 |

Apparatus for Vapor Deposition Polymerization Process

Figure 1:
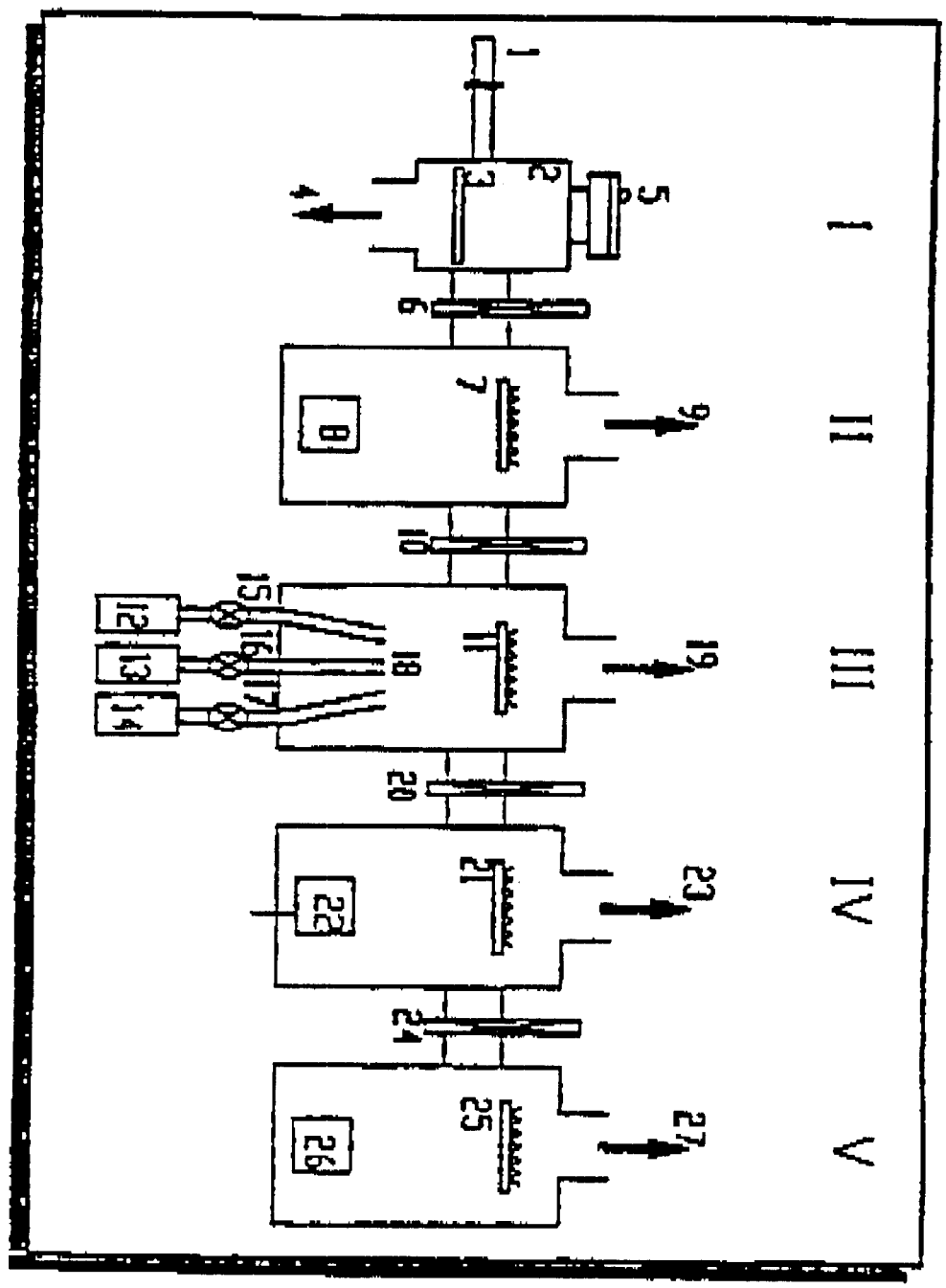
FIG. 1 is a schematic diagram of an apparatus for preparing the organic electroluminescent device of the present invention.

FIG. 1 is a schematic diagram of an apparatus for practicing one aspect of the present invention, which comprises loadlock chamber(I) equipped with magnetic bar (1) and quick access door(5) for loading a substrate; precleaning chamber(II) equipped with ion source(8); hole transport layer fabricating chamber(III) equipped with three crucibles (12, 13, 14) which are connected to chamber(III) through mass flow controllers(15, 16, 17); organic luminescent layer fabricating chamber(IV) equipped with a crucible for organic luminescent material; and cathode coating chamber (V) equipped with electron beam evaporator(26), said chambers being connected by gate valves 6, 100, 200, 24), and being equipped with pumping ports(4, 9, 19, 23, 27) and sample holders(3, 7, 11, 21, 25).

One aspect of the process for preparing an organic electroluminescent device of the present invention can be carried out by employing the apparatus shown in FIG. 1, as follows.

An ITO glass substrate is placed in substrate holder(3) in loadlock chamber(I) through quick access door(5). After evacuating chamber(I) through the pumping port(4), gate valve(6) is opened so that the ITO glass substrate is transported to substrate holder(7) in chamber(II) using magnetic bar(1).

Magnetic bar(1) is then returned to its original position and gate valve(6) is closed. The substrate is cleaned in chamber(II) using ion source(8). The ion treatment may be carried out by direct $O_2^-$ ion irradiation or $Ar^+$ ion irradiation with blowing $O_2$ gas.

Gate valves(6, 100) were opened and the substrate is transported to substrate holder(11) in chamber(III) employing magnetic bar(1), and then, magnetic bar(1) is retrieved to its original position and gate valves(6, 10) are closed.

In chamber(III), crucibles(12, 13, 14), containing a dianhydride, a diamine and a hole transport agent, respectively, are each heated to a preset temperature to evaporate each compound(e.g.: dianhydride:160–200° C., diamine:140–180, the hole transport agent:180–300). Each of mass flow controllers(15, 16, 17) is controlled to deposit each compound on the substrate at a suitable rate. The dianhydride and diamine deposited on the substrate react to form a polyimide precursor layer containing the hole transport agent dispersed therein, followed by thermal imidization of the precursor layer to form a polyimide layer.

Then, the substrate is transported to sample holder(21) in organic electroluminescent layer-coating chamber(IV) equipped with effusion cell(22) and an electroluminescent material is deposited on the hole transport layer at a deposition rate of 0.3 Å/sec or lower.

Subsequently, the substrate is transported to sample older (25) in cathode coating chamber(V) and a metal is deposited employing thermal evaporator or electron beam evaporator (26) to form a metal layer of the device.

In the above steps, the mass flow controllers are accurately controlled to adjust the composition ratio of the reactants by a feedback process which employs a residual gas analyzer and thickness monitor(not shown in FIG. 1).

The apparatus of the present invention mentioned above may be modified depending on the specific structure of the organic interlayer. For example, when an organic luminescent layer comprising a polyimide matrix is to be prepared, a dianhydride, a diamine and an organic luminescent material may be placed in the crucibles in chamber(III).

The apparatus of the present invention has advantages in that: the process is simple, contamination e.g., by an organic solvent can be avoided, and the layer thickness can be accurately controlled.

Multi-layer Structure

As mentioned above, the organic layer of the inventive organic electroluminescent device comprising an organic luminescent material, hole transport agent and/or electron transport agent may be in the form of a single layer or multiple layers.

Further, organometallic chelate complexes such as tris(8-hydroxyquinolinolato) aluminum($Alq_3$) which have both electroluminescent and electron transporting abilities may be dispersed in a polyimide matrix by a procedure similar to hat used in the preparation of organic luminescent layer to form a single layer of organic luminescent/electron transport layer.

Also a small amount of an electroluminescent material may be added to the hole transport layer so that holes can be readily injected into the organic luminescent layer when the device is in operation. Further, when an electron transport layer is employed in the organic electroluminescent device of the present invention, an organic luminescent material may be added to the electron transport layer in order to improve the injection of electron into the organic luminescent layer.

Figure 2:
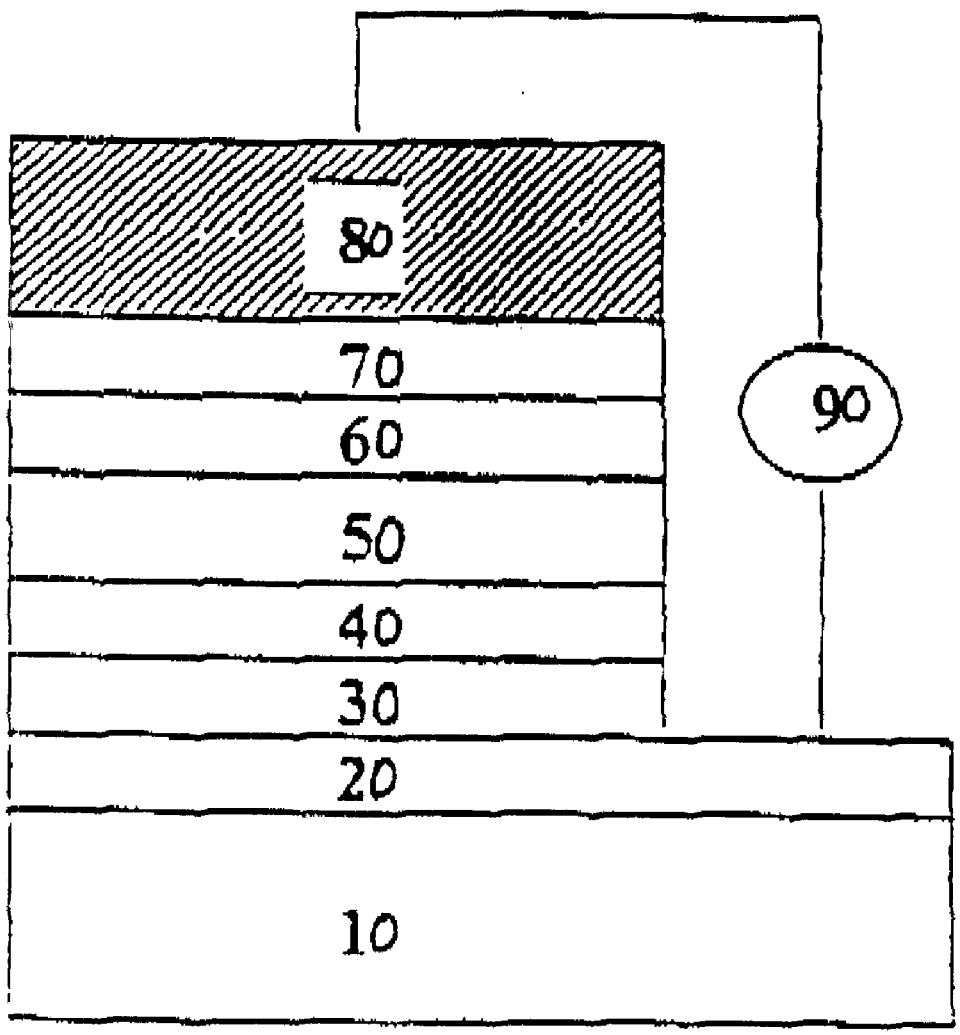
FIG. 2 illustrates a schematic diagram of an organic electroluminescent device prepared in accordance with one embodiment of the present invention.

Referring to FIG. 2, the organic electroluminescent device prepared in accordance with one aspect of the present invention comprises a transparent substrate(10), a transparent electrode layer(20), optional polyimide interfacial coupling layers(30, 70), a hole transport layer(40), an organic luminescent layer(50), an electron transport layer(60) and a metallic electrode(80). The electric power (90) may be an alternating current or direct current.

Formation of Distributed Bragg Reflector

In practicing the present invention, a set of polyimide thin layers may be additionally introduced as a distributed Bragg reflector(DBR) between the transparent substrate and the ITO thin film of the transparent electrode in order to amplify a specific wavelength of the emitted light, thereby further increasing the light emitting efficiency.

The DBR of the present invention has alternating layers of a polyimide film having a high refractive index and a polyimide film having a low refractive index, and may be prepared by suitably repeating the steps of vapor deposition polymerization of a dianhydride and a diamine to form a polyimide precursor layer, thermal imidization of the polyimide precursor layer, vapor deposition polymerization of a second dianhydride and a second diamine to form a second polyimide precursor layer on top of the polyimide layer, and thermal imidization of the second polyimide precursor layer.

Refractive indexes of representative polyimides are shown in Table II.

TABLE II

| Polyimide: dianhydride + diamine | Dielectric constant | Refractive index |
|---|---|---|
| PMDA + ODA | 3.22 | 1.80 |
| BTDA + 4,4'-ODA | 3.15 | 1.78 |
| BTDA + 3,3'-ODA | 3.09 | 1.76 |
| ODPA + 4,4'-ODA | 3.07 | 1.75 |
| ODPA + 3,3'-ODA | 2.99 | 1.73 |
| 6FDA + 4,4'-ODA | 2.79 | 1.67 |
| 6FDA + 3,3'-ODA | 2.73 | 1.65 |
| 6FDA + 6FDAM | 2.39 | 1.54 |

The reflective ratio of a DBR may be calculated in accordance with the following equation 1(see G. R. Fowles, Introduction to modern optics, New York; Holt, Rinehart and Winston, INC., 1968):

$$R = \left[ \frac{(n'/n'')^{2N} - 1}{(n'/n'')^{2N} + 1} \right]^2$$

wherein,
- n' is a refractive index of the polyimide layer having a high refractive index;
- n" is a refractive index of the polyimide layer having a low refractive index; and
- N is a number of the pairs of the polyimide layers.

For example, when ten pairs of a polyimide layer having a refractive index of 1.80, made from PMDA and ODA, and a polyimide layer having a refractive index of 1.54, made from 6FDA and 6FDAM, are fabricated to form a distributed Bragg reflector having a thickness of 115 nm, the reflective ratio of the reflector is calculated as 0.84. That is, the set of the polyimide layers acts as a high reflective mirror and form a flat planar microcavity structure together with the perfect mirror of the metallic electrode on the opposite side, thereby amplifying a specific wavelength of the emitted light and increasing the luminous efficiency of the device. Therefore, when a DBR is introduced between a transparent substrate and a transparent electrode layer, the device can be successfully applied to laser diode(see A. Dodabalapur et al., *J. Applied Phys.*, 80(12), p6953(1996)).

Preferred Embodiments

The preferred embodiments of the present invention are as follows:

A process for the preparation of an organic electroluminescent device in accordance with one aspect of the present invention, wherein the hole transport layer is prepared by vapor deposition polymerization of a hole transporting agent, a dianhydride and a diamine in a molar ratio ranging from 1:2:2 to 2:1:1 under a deposition rate ranging from 0.1 to 0.2 Å/sec, respectively.

A process for the preparation of an organic electroluminescent device in accordance with another aspect of the present invention, wherein the organic luminescent layer is prepared by vapor deposition polymerization of a organic luminescent material, a dianhydride and a diamine in a molar ratio ranging from 1:2:2 to 2:1:1 under a deposition rate ranging from 0.1 to 0.2 Å/sec, respectively.

In practicing the present invention, one or more additional polyimide interfacial coupling layers may be coated on the anode and/or before coating the cathode in order to reduce the contact resistance as well as to improve physical adhesion between metal and organic layers.

Further, the organic electroluminescent device of the present invention may be encased with a polyimide film. Generally, an organic electroluminescent device is packaged with a resin by a melt process, a wet process or a UV-cure method. However, in case a resin suitable for a melt process or a UV-curable polymer is used, the organic electroluminescent device may be undergo rapid aging due to the poor thermal stability of the encasing resin. When a wet process is employed, the solvent used therein may permeate into the device, thereby deteriorating the quality of the device. In order to solve the above problem, the organic electroluminescent device of the present invention may be encased with a polyimide film by vapor deposition polymerization of a dianhydride and a diamine, followed by a thermal imidization. The inventive device encased with a polyimide film is highly stable due to the protection thereof against air and moisture.

In organic electroluminescent device of the present invention having a single or multiple organic layers, a polyimide layer can be utilized in one or more organic layers to increase the stability, luminous efficiency and lifetime of the device. Particularly, when the organic interlayer is in the form of polyimide/polyimide double layer, the physical stability of the device can be greatly improved. Further, the emitted light can be shifted to a shorter wavelength by controlling either the amount of organic luminescent material dispersed in a polyimide or the applied voltage.

An organic electroluminescent device can be prepared in the form of a flat panel display in accordance with the present invention. Further, when one or more polyimide layers are used in all organic layers together with a flexible electrode, a flexible display may be also manufactured. Also, the organic layers of the present invention may be applied to laser diodes, solar cells, field effect transistors, photodiodes, photorefractive optical memory device and the like.

The present invention is further described and illustrated in Examples, which are, however, not intended to limit the scope of the present invention.

EXAMPLE 1

Indium-tin-oxide(ITO) was coated on a glass substrate to form a transparent anode layer. The coated substrate was washed successively with a neutral and non-phosphorous Extran(DuPont) solution, acetone and ethanol by employing an ultrasonicator and then stored in ethanol.

The substrate was positioned in a sample holder in an organic luminescent layer fabricating chamber and 0.05 g of each of 4-(dicyanomethylene)-2-methyl-6-(4-dimethylaminostyryl)-4H-pyran(DCM), pyromellitic dianhydride(PMDA) and 4,4-oxyphenylene diamine(ODA) were added to respective crucibles. The inner pressure of the organic luminescent layer fabricating chamber was reduced to $1.0 \times 10^{-6}$ torr and each crucible was heated to a preset temperature(PMDA:180° C., ODA:160° C. and DCM:220–230° C.). The evaporation rate of each of PMDA, ODA and DCM was controlled within the range from 0.1 to 0.2 Å/sec by employing a thickness monitor(STM 100/MF) equipped with a quartz oscillator.

When the desired evaporation rate was attained, the vapor deposition was carried out to deposit a poly(amic acid) layer containing DCM to a thickness of 300 to 320 Å.

Then, the resulting substrate was placed in a vacuum oven and the oven temperature was raised at a rate of 2° C./min to 170° C. and held at 170° C. for 1 hour.

Subsequently, aluminum was deposited on the organic luminescent layer under a chamber pressure of $2 \times 10^{-6}$ torr to form an aluminum electrode having a thickness of 3,000 Å.

The turn-on voltage of the device thus obtained was 8.0V.

Figure 3:
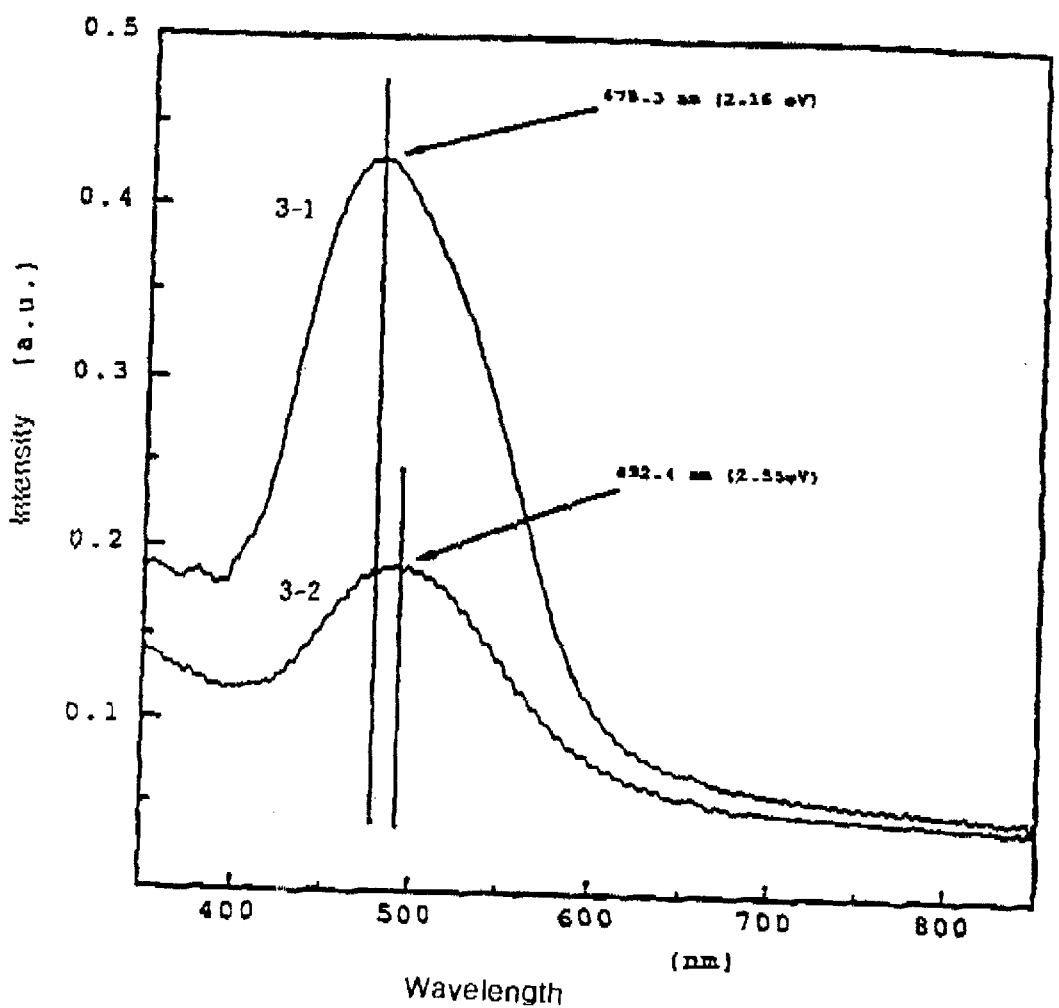
FIG. 3 shows UV-visible absorption spectra of a DCM/PMDA-ODA layer(FIG. 3-1: before thermal imidization.

FIG. 3 shows the UV-visible absorption spectrum of the DCM/PMDA-ODA layer(3-1: before the thermal imidization; 3-2: after the thermal imidization). As can be seen in FIG. 3, the thermal imidization brought about a shift in $\lambda_{max}$ from 478.3 nm(2.16 eV) to 492.4 nm(2.55 eV). This shift suggests that DCM molecules are more closely packed due to the increased density of the organic layer after the thermal imidization.

EXAMPLE 2

Indium-tin-oxide(ITO) was coated on a glass substrate to form a transparent anode layer. The coated substrate was washed successively with a neutral and non-phosphorous Extran(DuPont) solution, acetone and ethanol by employing an ultrasonicator and then stored in ethanol.

Referring to the apparatus of FIG. 1, washed substrate was positioned in sample holder(11) and 0.05 g each of N,N'-diphenyl-N,N'-bis(3-methylphenyl)-1,1-diphenyl-4,4'-diamine(TPD), PMDA and ODA were added to respective crucibles(12, 13, 14). The inner pressure of chamber (III) was reduced to $1.0 \times 10^{-6}$ torr and each crucible was heated to a preset temperature (PMDA: 180° C., ODA:160° C. and TPD:220° C.). The evaporation rate of each of PMDA, ODA and TPD was controlled within the range from 0.1 to 0.2 Å/sec by employing a thickness monitor(STM 100/MF) equipped with a quartz oscillator.

When the desired evaporation rate was attained, the vapor deposition was carried out until the thickness of poly(amic acid) layer containing TPD reached 450 to 525 Å.

Then, the substrate was placed in a vacuum oven, and the oven temperature was raised at a rate of 2° C./min to 200° C. and held at 200° C. for 1 hour.

Subsequently, $Alq_3$ was deposited to form an organic luminescent layer having a thickness of 300 Å. Then, aluminum was deposited to form an aluminum electrode having a thickness of 3,500 Å.

The turn on voltage of the device thus obtained is shown in Table III.

Figures 1, 4:
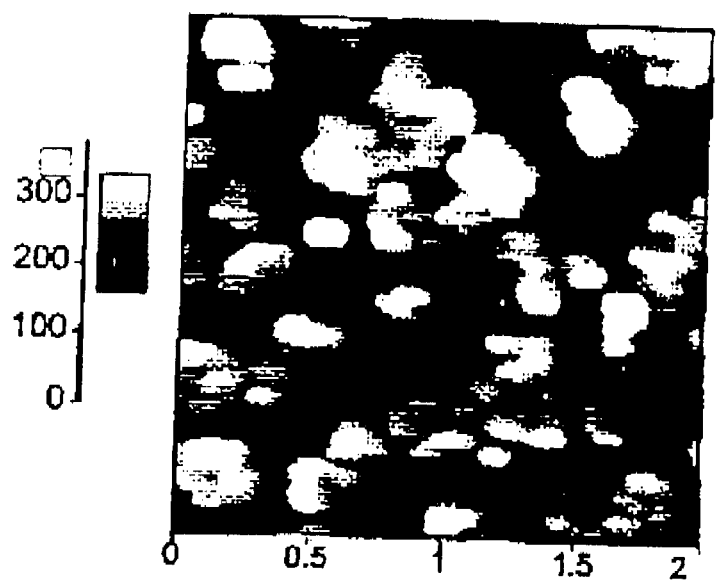
Figures 2, 4:
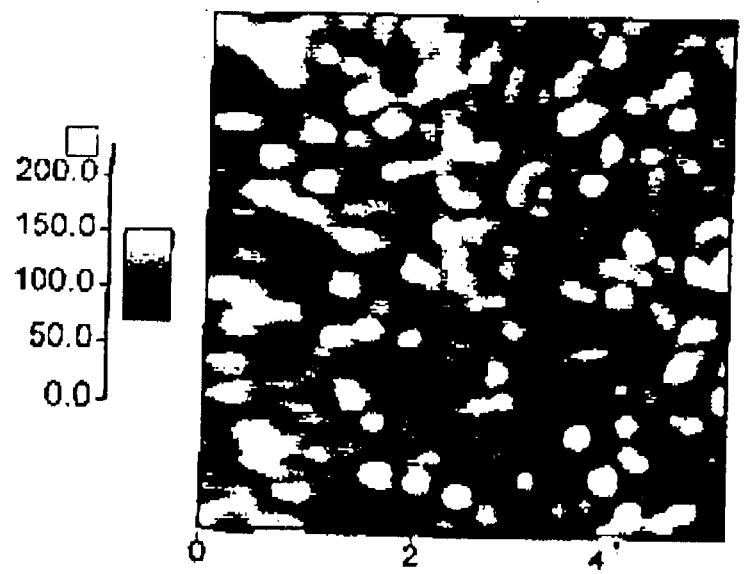

FIGS. 4-1 and 4-2 depict the atomic force microscopic spectra of the surface morphologies of a commercial ITO layer and the hole transport layer formed above, respectively. The root mean square roughness of the surface of the ITO layer was 54.9 Å, while that of the surface of the hole transport layer formed above was 26.4 Å, i.e., about 48% of that of the ITO layer. This result suggests that when the vapor deposition polymerization process of the present invention is employed, more uniform layer can be formed.

EXAMPLES 3–10

The procedure of Example 2 was repeated except that the conditions were varied as shown in Table III. The turn-on voltages of the devices obtained in these Examples are shown in Table III.

The device prepared in Example 7 has high luminous efficiency, i.e., 12 lm/W.

Comparative Examples 1–6

The procedure of Example 2 was repeated except that the conditions were varied as shown in Table III.

The turn-on voltages of the devices are shown in Table III.

TABLE III

| | PMDA:ODA:TPD | HTL (Å) | ELL (Å) | Heat Treatment | Turn-on Voltage |
|---|---|---|---|---|---|
| Ex. 2 | 2:2:1 | 347 | 300 | o | 8.7 |
| Ex. 3 | 1:1:1 | 347 | 300 | o | 8.6 |
| Ex. 4 | 1:1:2 | 347 | 300 | o | 10.4 |
| Ex. 5 | 2:2:1 | 250 | 300 | o | 6.6 |
| Ex. 6 | 1:1:1 | 250 | 200 | o | 5.8 |
| Ex. 7 | 1:1:2 | 250 | 200 | o | 5.7 |
| Ex. 8 | 2:2:1 | 250 | 300 | o | 8.17 |
| Ex. 9 | 1:1:1 | 250 | 300 | o | 7.05 |
| Ex. 10 | 1:1:2 | 250 | 300 | o | 6.54 |
| Comp. Ex. 1 | 2:2:1 | 525 | 300 | x | 8.9 |
| Comp. Ex. 2 | 1:1:1 | 525 | 300 | x | 10.2 |
| Comp. Ex. 3 | 1:1:2 | 525 | 300 | x | 11.5 |

TABLE III-continued

| | PMDA:ODA:TPD | HTL (Å) | ELL (Å) | Heat Treatment | Turn-on Voltage |
|---|---|---|---|---|---|
| Comp. Ex. 4 | 2:2:1 | 450 | 200 | x | 7.66 |
| Comp. Ex. 5 | 1:1:1 | 450 | 200 | x | 5.64 |
| Comp. Ex. 6 | 1:1:2 | 450 | 200 | x | 6.28 | note:
HTL: Hole Transport Layer
ELL: Electroluminescent Layer
LE: Luminous Efficiency

EXAMPLE 11

The device prepared in Example 1 was placed in a sample holder and PMDA and ODA were vapor deposited thereon at 185° C. for PMDA and 155° C. for ODA to encapsulate the device.

EXAMPLE 12

ITO was coated on a glass substrate to form a transparent anode layer.

0.01 g each of ODPA, ODA and TPD were positioned in respective crucibles and the vapors thereof were deposited on the anode layer under the pressure of $2 \times 10^{-4}$ torr at 180° C. for ODPA, 160° C. for ODA and 220° C. for TPD to form a poly(amic acid) layer containing TPD. The poly(amic acid) layer was heat treated at 180° C. for 1 hour to form a hole transport layer having a thickness of 180 Å.

Subsequently, Alq3 was deposited to form an organic luminescent layer having a thickness of 200 Å. Then, aluminum was deposited to form an aluminum electrode having a thickness of 3,000 Å.

The turn on voltage of the device thus obtained was 5V; and the luminous efficiency thereof at 9V was 13 lm/W.

EXAMPLE 13

The procedure of Example 12 was repeated except that the thickness of the hole transport layer was 150 Å.

The turn on voltage of the device thus obtained was 4V; and the luminous efficiency thereof at 8V was 23 lm/W.

As shown in the above result, the luminous efficiency of the device prepared in accordance with the present invention is greatly improved. Further, the polyimide layer exhibits a high density and uniform thickness. Therefore, the vapor deposition polymerization process of the present invention may be advantageously applied to solar cells, field effect transistors, photodiodes and the like.

While the embodiments of the subject invention have been described and illustrated, it is obvious that various changes and modifications can be made therein without departing from the spirit of the present invention which should be limited only by the scope of the appended claims.

What is claimed is:

1. A process for preparing an organic electroluminescent device having a transparent substrate, a transparent electrode layer, a metallic electrode layer, and an organic interlayer disposed between and in close contact with the electrode layers, the organic interlayer being comprised of an organic luminescent layer, an optional hole transport layer and a optional electron transport layer and containing an electronically active material dispersed in a matrix of polyimide of formula (I), characterized in that the organic interlayer is prepared by depositing the vapors of a dianhydride, a diamine and the electronically active material to form a polyimide precursor layer containing the active material dispersed therein; and thermally imidizing the polyimide precursor layer, comprising:

repeating the steps of i) vapor deposition polymerization of a first dianhydride and a first diamine to fabricate a first polyimide precursor layer, ii) thermal imdization of the first precursor layer to fabricate a first polyimide layer, iii) vapor deposition polymerization of a second dianhydride and a second diamine to fabricate a second polyimide precursor layer, and iv) thermal imidization of the second precursor layer to fabricate a second polyimide layer, to form a distributed Bragg reflector having an alternately stacked structure of the first polyimide layer and the second polyimide layer having a refractive index lower than that of the first polyimide film, the distributed Bragg reflector being positioned between the transparent substrate and the transparent electrode:

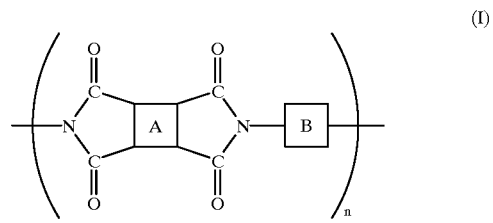

(I)

wherein A is derived from the dianhydride; B is derived from the diamine; and n is an integer of 2 or higher.

* * * * *